United States Patent
Yeadon

(10) Patent No.: US 6,974,803 B2
(45) Date of Patent: Dec. 13, 2005

(54) PHARMACEUTICAL COMBINATION

(75) Inventor: Michael Yeadon, Sandwich (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/308,160

(22) Filed: Dec. 2, 2002

(65) Prior Publication Data

US 2003/0139369 A1 Jul. 24, 2003

Related U.S. Application Data

(60) Provisional application No. 60/352,465, filed on Jan. 28, 2002.

(30) Foreign Application Priority Data

Dec. 6, 2001 (GB) .................................. 0129270

(51) Int. Cl.⁷ .................. A01N 43/04; A61K 31/70; A61K 31/135
(52) U.S. Cl. ............... 514/46; 514/42; 514/43; 514/45; 514/653; 514/826; 536/27.1; 536/27.13; 536/27.2; 536/27.21; 424/45; 424/46
(58) Field of Search ............... 514/42, 43, 45, 514/46, 653, 826; 536/27.1, 27.13, 27.2, 27.21; 424/45, 46

(56) References Cited

U.S. PATENT DOCUMENTS 6,143,277 A * 11/2000 Ashurst et al. ............... 424/45
6,753,322 B2 * 6/2004 Mantell et al. ............... 514/46
2002/0058641 A1 * 5/2002 Mantell et al. ............... 514/46

FOREIGN PATENT DOCUMENTS

| WO | WO9967263 | 12/1999 | ........... C07H/19/16 |
| WO | WO0194368 | 12/2001 | ......... C07H/19/167 |

OTHER PUBLICATIONS

Berge et al., J. Pharm. Sci, 66, 1–19, 1977.

Sandford et al., Eur. Respir. J., 10, 1380–1391, 1997.

Thomas Giangrasso, *Potential for Tolerance, Morbidity, and Mortality Resulting From Regular Use of b2–Adrenergic Agonists in Asthma*, Southern Medical Journal, vol. 90, No. 2, pp. 173–179 (Feb. 1997).

\* cited by examiner

*Primary Examiner*—James O. Wilson
*Assistant Examiner*—Traviss C. McIntosh, III
(74) *Attorney, Agent, or Firm*—Peter C. Richardson; Gregg C. Benson; William F. Mulholland

(57) ABSTRACT

The present invention relates to a combination comprising (a) an adenosine $A_{2a}$ receptor agonist as defined herein and (b) an adrenergic β2 receptor agonist, for simultaneous, sequential or separate administration by the inhaled route in the treatment of an obstructive airways or other inflammatory disease.

30 Claims, No Drawings

PHARMACEUTICAL COMBINATION

CROSS REFERENCE TO RELATED APPLICATIONS

This application is filed claiming priority to U.S. Provisional Application No. 60/352,465, filed Jan. 28, 2002.

The present invention relates to an inhaled combination of an adenosine $A_{2a}$ receptor agonist and an adrenergic β2 receptor agonist, to pharmaceutical compositions, including devices for administering, and to the uses of such a combination.

A combination of an adenosine $A_{2a}$ receptor agonist and an adrenergic β2 receptor agonist is useful in the treatment of obstructive airways and other inflammatory diseases, particularly the obstructive airways diseases asthma, chronic obstructive pulmonary disease (COPD) and other obstructive airways diseases exacerbated by heightened bronchial reflexes, inflammation, bronchial hyper-reactivity and bronchospasm.

Examples of particular diseases that may be treated with the present invention include the respiratory diseases asthma, acute respiratory distress syndrome, chronic pulmonary inflammatory disease, bronchitis, chronic bronchitis, chronic obstructive pulmonary (airway) disease and silicosis and diseases of the immune system such as allergic rhinitis and chronic sinusitis.

Adenosine has a wide range of physiologic activities, including immune and inflammatory responses, which are receptor-mediated and involve interaction with at least four types of plasma membrane receptors. These receptors are commonly referred to as $A_1$, $A_{2a}$, $A_{2b}$, and $A_3$. Adenosine and its analogs have been found to possess a broad spectrum of anti-inflammatory activity that involves a significant variety of immune and inflammatory cells, including neutrophils and eosinophils. Activation of the $A_{2a}$ receptors on neutrophils results in the suppression of the production of reactive oxidants and other mediators of inflammation such as elastase by these cells, as well as decreased expression of $β_2$-integrins.

$A_{2a}$ receptors are known to exist on lymphocytes, neutrophils, eosinophils, basophils, monocytes/macrophages, epithelial cells, and on the vascular endothelial tissue with which they interact. Adenosine binding to $A_{2a}$ receptors can decrease inflammation by influencing the activities of a number of these cell types. For example, $A_{2a}$ receptor agonists markedly inhibit oxidative species elicited by physiologic stimulants such as neutrophil chemoattractants, cytokines, and lipid products.

Occupancy of adenosine $A_{2a}$ receptors stimulates neutrophil adenylyl cyclase, which results in an increase in intracellular cyclic AMP. In turn, increased neutrophil cyclic AMP results in depression of stimulated-neutrophil oxidative activity. Through a related action on a variety of other inflammatory cell types, the anti-inflammatory properties of $A_{2a}$ agonists extends beyond inhibitory activities on neutrophils. Adenosine also decreases endotoxin-stimulated monocyte/macrophage TNFα release, and it has been observed that endogenous adenosine as well as adenosine analogs reduce human monocyte TNFα production by binding to adenosine $A_{2a}$ receptors.

Endotoxin-stimulated release of interleukin-6 (IL-6) and interleukin-8 (IL-8) is decreased by adenosine analogs with an order of potency that suggests $A_{2a}$ adenosine receptor activity. Interleukin-10 (IL-10) has anti-inflammatory activity as a result of its ability to decrease endotoxin-stimulated TNFα release from monocytes, to inhibit oxidative activity, and to lower the expression of leukocyte adhesion molecules. Adenosine enhances stimulated human monocyte production of IL-10; consequently, the binding of adenosine at $A_{2a}$ receptors promotes resolution of any on-going inflammatory response that may be involved.

Activated eosinophils transmigrate into tissues and cause cellular damage and inflammation in such diseases as allergic and non-allergic asthma, allergic rhinitis, and atopic dermatitis. Adenosine and adenosine $A_{2a}$ receptor agonist analogs, by binding to $A_{2a}$ receptors on eosinophils, inhibit stimulated release of reactive oxygen species, a response which parallels the inhibitory effect of $A_{2a}$ receptors on neutrophils.

Further, inhaled $A_{2a}$ agonists inhibit the recruitment of eosinophils into lungs of sensitised guinea-pigs via action in the lungs (see WO-A-99/67263). This is important as $A_{2a}$ agonists relax blood vessels and lower blood pressure in animals thus the anti-inflammatory action of $A_{2a}$ agonists is ideally produced by an inhaled agent which has a high therapeutic index for activity in the lung compared with the peripheral compartment.

Adrenergic β receptors occur in the sympathetic nervous system. There are at least two types. Adrenergic β1 receptors are found in the heart and play a major role in regulating heart rate via the action of the agonists epinephrine and norepinephrine. Adrenergic β2 receptors are present on a number of cell types in the lung (e.g. airway smooth muscle cells, epithelial cells, and a variety of inflammatory cells) and adrenergic β2 receptor agonists are effective bronchdilators, causing the relaxation of airway smooth muscle. Sympathomimetic amines have a long history of use in the treatment of chronic airway diseases characterised by partially reversible airway narrowing such as COPD and asthma and were first used as bronchodilators in the form of intravenous epinephrine. Later, inhaled β-adrenergic agents such as isoprenaline were used which were relatively non-selective for β2 over β1 receptors and thus caused tachycardia at effective bronchodilator doses. More recently, inhaled β-adrenergic agents such as salbutamol have been used which are more selective for the β2 receptor but short-acting. Inhaled β-adrenergic agents formoterol and salmeterol are both selective and long-acting.

It has now been surprisingly found that combinations of particular adenosine $A_{2a}$ receptor agonists and adrenergic β2 receptor agonists offer significant benefits in the treatment of obstructive airways and other inflammatory diseases over treatment with either agent alone and over other known combinations. The advantage of the combination is to provide optimal control of airway calibre through the mechanism most appropriate to the disease pathology, namely adrenergic β2 receptor agonism, together with effective suppression of inappropriate inflammation. In this way, symptoms of the disease are controlled by correcting inappropriate airway neural reflexes which drive cough, mucus production and dyspnea. By delivering both an adrenergic β2 receptor agonist and an $A_{2a}$ agonist via the inhaled route, the benefits of each class are realised without the unwanted peripheral effects. Further, the particular combinations of the present invention result in unexpected synergy, producing greater efficacy than maximally tolerated doses of either class of agent used alone.

The invention therefore provides an inhaled combination of (a) an adenosine $A_{2a}$ receptor agonist of the formula

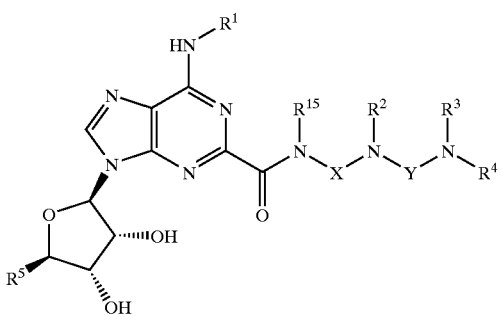

(I)

or a pharmaceutically acceptable salt or solvate thereof, wherein $R^1$ is H, $C_1$–$C_6$ alkyl or fluorenyl, said $C_1$–$C_6$ alkyl being optionally substituted by 1 or 2 substituents each independently selected from phenyl and naphthyl, said phenyl and naphthyl being optionally substituted by $C_1$–$C_6$ alkyl, $C_1$–$C_6$ alkoxy, halo or cyano;

(A) $R^2$ is H or $C_1$–$C_6$ alkyl, $R^{15}$ is H or $C_1$–$C_6$ alkyl, and X is either (i) unbranched $C_2$–$C_3$ alkylene optionally substituted by $C_1$–$C_6$ alkyl or $C_3$–$C_8$ cycloalkyl, or (ii) a group of the formula:

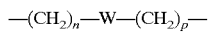

where W is $C_5$–$C_7$ cycloalkylene optionally substituted by $C_1$–$C_6$ alkyl, n is 0 or 1 and p is 0 or 1, or (B) $R^{15}$ is H or $C_1$–$C_6$ alkyl, and $R^2$ and X, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl, or (C) $R^2$ is H or $C_1$–$C_6$ alkyl, and $R^{15}$ and X, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl;

either, $R^3$ and $R^4$, taken together with the nitrogen atom to which they are attached, represent azetidinyl, pyrrolidinyl, piperidinyl, piperazinyl, homopiperidinyl or homopiperazinyl, each being optionally substituted on a ring nitrogen or carbon atom by $C_1$–$C_6$ alkyl or $C_3$–$C_8$ cycloalkyl and optionally substituted on a ring carbon atom not adjacent to a ring nitrogen atom by —$NR^6R^7$, or, $R^3$ is H, $C_1$–$C_6$ alkyl, $C_3$–$C_8$ cycloalkyl or benzyl and $R^4$ is (a) azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl, $C_3$–$C_8$ cycloalkyl, phenyl, benzyl or het, or (b) —($C_2$–$C_6$ alkylene)-$R^8$, (c) —($C_1$–$C_6$ alkylene)-$R^{13}$, or (d) $C_1$–$C_6$ alkyl or $C_3$–$C_8$ cycloalkyl;

$R^5$ is $CH_2OH$ or $CONR^{14}R^{14}$;

$R^6$ and $R^7$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl;

$R^8$ is (i) azetidin-1-yl, pyrrolidin-1-yl, piperidin-1-yl, morpholin-4-yl, piperazin-1-yl, homopiperidin-1-yl, homopiperazin-1-yl or tetrahydroisoquinolin-1-yl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^9R^9N$—($C_1$–$C_6$)-alkyl, fluoro-($C_1$–$C_6$)-alkyl, —$CONR^9R^9$, —$COOR^9$ or $C_2$–$C_5$ alkanoyl, and optionally substituted on a ring carbon atom not adjacent to a ring nitrogen atom by fluoro-($C_1$–$C_6$)-alkoxy, halo, —$OR^9$, cyano, —$S(O)_mR^{10}$, —$NR^9R^9$, —$SO_2NR^9R^9$, —$NR^9COR^{10}$ or —$NR^9SO_2R^{10}$, and said piperazin-1-yl and homopiperazin-1-yl being optionally substituted on the ring nitrogen atom not attached to the $C_2$–$C_6$ alkylene group by $C_1$–$C_6$ alkyl, phenyl, $C_1$–$C_6$ alkoxy-($C_2$–$C_6$)-alkyl, $R^9R^9N$—($C_2$–$C_6$)-alkyl, fluoro-($C_1$–$C_6$)-alkyl, $C_2$–$C_5$ alkanoyl, —$COOR^{10}$, $C_3$–$C_8$ cycloalkyl, —$SO_2R^{10}$, —$SO_2NR^9R^9$ or —$CONR^9R^9$, or (ii) $NR^{11}R^{12}$;

$R^9$ is H, $C_1$–$C_6$ alkyl, $C_3$–$C_8$ cycloalkyl or phenyl;

$R^{10}$ is $C_1$–$C_6$ alkyl, $C_3$–$C_8$ cycloalkyl or phenyl;

$R^{11}$ is H, $C_1$–$C_6$ alkyl, $C_3$–$C_8$ cycloalkyl or benzyl;

$R^{12}$ is H, $C_1$–$C_6$ alkyl, $C_3$–$C_8$ cycloalkyl, phenyl, benzyl, fluoro-($C_1$–$C_6$)-alkyl, —$CONR^9R^9$, —$COOR^{10}$, $C_2$–$C_5$ alkanoyl or —$SO_2NR^9R^9$;

$R^{13}$ is (a) phenyl, pyridin-2-yl, pyridin-3-yl or pyridin-4-yl, each being optionally substituted by $C_1$–$C_6$ alkyl, $C_1$–$C_6$ alkoxy, —($C_1$–$C_3$ alkylene)-($C_1$–$C_6$ alkoxy), halo, cyano, —($C_1$–$C_3$ alkylene)-CN, —$CO_2H$, —($C_1$–$C_3$ alkylene)-$CO_2H$, —$CO_2$($C_1$–$C_6$ alkyl), —($C_1$–$C_3$ alkylene)-$CO_2$ ($C_1$–$C_6$ alkyl), —($C_1$–$C_3$ alkylene)-$NR^{14}R^{14}$, —$CONR^{14}R^{14}$ or —($C_1$–$C_3$ alkylene)-$CONR^{14}R^{14}$, or (b) azetidin-2-yl, azetidin-3-yl, pyrrolidin-2-yl, pyrrolidin-3-yl, piperidin-2-yl, piperidin-3-yl, piperidin-4-yl, homopiperidin-2-yl, homopiperidin-3-yl or homopiperidin-4-yl, each being optionally substituted by $C_1$–$C_6$ alkyl, $C_3$–$C_8$ cycloalkyl, phenyl, benzyl or het;

$R^{14}$ is H or $C_1$–$C_6$ alkyl optionally substituted by cyclopropyl;

m is 0, 1 or 2;

Y is CO, CS, $SO_2$ or C=N(CN); and

"het", used in the definition of $R^4$ and $R^{13}$, is a C-linked, 4- to 6-membered ring, heterocycle having either from 1 to 4 ring nitrogen heteroatoms or 1 or 2 nitrogen ring heteroatoms and 1 oxygen or 1 sulphur ring heteroatom, optionally substituted by $C_1$–$C_6$ alkyl, $C_3$–$C_8$ cycloalkyl, $C_1$–$C_6$ alkoxy, $C_3$–$C_8$ cycloalkoxy, hydroxy, oxo or halo;

and (b) an adrenergic β2 receptor agonist.

Further, the invention provides an inhaled combination comprising (a) an adenosine $A_{2a}$ receptor agonist of the formula (I), as defined above and (b) an adrenergic β2 receptor agonist, for use as a medicament.

Further, the invention provides a combination comprising (a) an adenosine $A_{2a}$ receptor agonist of the formula (I), as defined above and (b) an adrenergic β2 receptor agonist, for simultaneous, sequential or separate administration by the inhaled route in the treatment of an obstructive airways or other inflammatory disease.

Further, the invention provides a pharmaceutical composition comprising an adenosine $A_{2a}$ receptor agonist of the formula (I), as defined above, an adrenergic β2 receptor agonist and a pharmaceutically acceptable excipient, diluent or carrier, for administration by the inhaled route in the treatment of an obstructive airways or other inflammatory disease.

Further, the invention provides the use of an adenosine $A_{2a}$ receptor agonist of the formula (I), as defined above, or an adrenergic β2 receptor agonist, in the manufacture of a medicament for simultaneous, sequential or separate administration of both agents by the inhaled route in the treatment of an obstructive airways or other inflammatory disease.

Further, the invention provides a method of treating of an obstructive airways or other inflammatory disease comprising administering simultaneously, sequentially or separately, by the inhaled route, to a mammal in need of such treatment, an effective amount of an adenosine $A_{2a}$ receptor agonist of the formula (I), as defined above and an adrenergic β2 receptor agonist.

Further, the invention provides an inhalation device for simultaneous, sequential or separate administration of an adenosine $A_{2a}$ receptor agonist of the formula (I), as defined above and an adrenergic β2 receptor agonist, in the treatment of an obstructive airways or other inflammatory disease.

The preparation of a compound of the formula (I) is described in International Patent Application number PCT/IB01/00973, published as WO-A-01/94368.

Preferred adenosine $A_{2a}$ receptor agonists for use in the invention include 6-[(2,2-diphenylethyl)amino]-9-{(2R,3R,4S,5S)-5-[(ethylamino)carbonyl]-3,4-dihydroxytetrahydro-2-furanyl}-N-{2-[({[1-(2-pyridinyl)-4-piperidinyl]amino}carbonyl)amino]ethyl}-9H-purine-2-carboxamide (Examples 8 and 35 of WO-A-01/94368) and the pharmaceutically acceptable salts and solvates thereof.

Preferably, an adrenergic β2 receptor agonist used in a combination according to the invention is a selective adrenergic β2 receptor agonist, i.e. has a greater affinity for the adrenergic β2 receptor than all other known adrenergic β receptors. Preferably, the affinity of such a selective adrenergic β2 receptor agonist is at least 100 fold greater for the adrenergic β2 receptor as compared with its affinity for the other adrenergic β receptors.

Preferred adrenergic β2 receptor agonists for use in the invention include salmeterol, formoterol and the pharmaceutically acceptable salts and solvates thereof.

Specific preferred combinations of an adenosine $A_{2a}$-receptor agonist and an adrenergic β2 receptor agonist for use in the invention include:

6-[(2,2-diphenylethyl)amino]-9-{(2R,3R,4S,5S)-5-[(ethylamino)carbonyl]-3,4-dihydroxytetrahydro-2-furanyl}-N-{2-[({[1-(2-pyridinyl)-4-piperidinyl]amino}carbonyl)amino]ethyl}-9H-purine-2-carboxamide, or a pharmaceutically acceptable salt or solvate thereof and salmeterol, or a pharmaceutically acceptable salt or solvate thereof; and 6-[(2,2-diphenylethyl)amino]-9-{(2R,3R,4S,5S)-5-[(ethylamino)carbonyl]-3,4-dihydroxytetrahydro-2-furanyl}-N-{2-[({[1-(2-pyridinyl)-4-piperidinyl]amino}carbonyl)amino]ethyl}-9H-purine-2-carboxamide, or a pharmaceutically acceptable salt or solvate thereof and formoterol, or a pharmaceutically acceptable salt or solvate thereof.

An adenosine $A_{2a}$ receptor agonist or adrenergic β2 receptor agonist used in accordance with the invention may optionally be utilised in the form of a pharmaceutically acceptable salt or solvate. Such a salt may be an acid addition or a base salt.

Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts.

Suitable base salts are formed from bases which form non-toxic salts and examples are the sodium, potassium, aluminium, calcium, magnesium, zinc and diethanolamine salts.

For a review on suitable salts see Berge et al, J. Pharm. Sci., 66, 1–19, 1977.

The pharmaceutically acceptable solvates of the adenosine $A_{2a}$ receptor agonists and adrenergic β2 receptor agonists used in accordance with the invention, or salts thereof, include the hydrates thereof.

The adenosine $A_{2a}$ receptor agonists and adrenergic β2 receptor agonists of the invention may exist in one or more polymorphic forms.

The adenosine $A_{2a}$ receptor agonists and adrenergic β2 receptor agonists of the invention may contain one or more asymmetric carbon atoms and therefore exists in two or more stereoisomeric forms (e.g. R, R' formoterol is a preferred embodiment). Where such an agonist contains an alkenyl or alkenylene group, cis/trans (or Z/E) isomerism may also occur. The present invention includes these individual stereoisomers of the compounds of the invention and, where appropriate, the individual tautomeric forms thereof, together with mixtures thereof.

Separation of diastereoisomers or cis and trans isomers may be achieved by conventional techniques, e.g. by fractional crystallisation, chromatography or H.P.L.C. of a stereoisomeric mixture of a compound of the invention or a suitable salt or derivative thereof. An individual enantiomer of a compound of the invention may also be prepared from a corresponding optically pure) intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

The present invention also includes all suitable isotopic variations of a compound of the invention or a pharmaceutically acceptable salt thereof. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that can be incorporated into compounds of the invention and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the compounds of the invention and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances.

The types of diseases that may be treated using the combinations of the present invention include, but are not limited to, asthma, chronic or acute bronchoconstriction, chronic bronchitis, small airways obstruction, emphysema, chronic obstructive pulmonary disease (COPD), COPD that has chronic bronchitis, pulmonary emphysema or dyspnea associated therewith and COPD that is characterised by irreversible, progressive airways obstruction.

Asthma

One of the most important respiratory diseases treatable with the combinations of therapeutic agents of the present invention is asthma, a chronic, increasingly common disorder encountered worldwide and characterized by intermittent reversible airway obstruction, airway hyperresponsiveness and inflammation. The cause of asthma has yet to be determined, but the most common pathological expression of asthma is inflammation of the airways, which may be significant even in the airways of patients with mild asthma. This inflammation drives reflex airway events resulting in plasma protein extravasation, dyspnea and bronchoconstriction. Based on bronchial biopsy and lavage studies it has been clearly shown that asthma involves infiltration by mast cells, eosinophils, and T-lymphocytes into a patient's airways. Bronchoalveolar lavage (BAL) in atopic asthmatics shows activation of interleukin (IL)-3, IL-4, IL-5 and granulocyte/macrophage-colony stimulating factor (GM-CSF) that suggests the presence of a T-helper 2 (Th-2)-like T-cell population.

The combinations of therapeutic agents of the present invention are useful in the treatment of atopic and non-atopic asthma. The term "atopy" refers to a genetic predisposition toward the development of type I (immediate) hypersensitivity reactions against common environmental antigens. The most common clinical manifestation is allergic rhinitis, while bronchial asthma, atopic dermatitis, and food allergy occur less frequently. Accordingly, the expression "atopic asthma" as used herein is intended to be synonymous with "allergic asthma", i.e., bronchial asthma which is an allergic manifestation in a sensitized person. The term "non-atopic asthma" as used herein is intended to refer to all other asthmas, especially essential or "true" asthma, which is provoked by a variety of factors, including vigorous exercise, irritant particles, psychologic stresses, etc.

Chronic Obstructive Pulmonary Disease (COPD)

The combinations of therapeutic agents of the present invention are still further useful in the treatment of COPD or COAD including chronic bronchitis, pulmonary emphysema or dyspnea associated therewith. COPD is characterized by poorly reversible, progressive airways obstruction. Chronic bronchitis is associated with hyperplasia and hypertrophy of the mucus secreting glands of the submucosa in the large cartilaginous airways. Goblet cell hyperplasia, mucosal and submucosal inflammatory cell infiltration, edema, fibrosis, mucus plugs and increased smooth muscle are all found in the terminal and respiratory bronchioles. The small airways are known to be a major site of airway obstruction. Emphysema is characterized by destruction of the alveolar wall and loss of lung elasticity. A number of risk factors have also been identified as linked to the incidence of COPD. The link between tobacco smoking and COPD is well established. Other risk factors include exposure to coal dust and various genetic factors. See Sandford et al., "Genetic risk factors for chronic obstructive pulmonary disease," *Eur. Respir. J.* 10 1380–1391, 1997. The incidence of COPD is increasing and it represents a significant economic burden on the populations of the industrialized nations. COPD also presents itself clinically with a wide range of variation from simple chronic bronchitis without disability to patients in a severely disabled state with chronic respiratory failure.

COPD is characterized by inflammation of the airways, as is the case with asthma, but the inflammatory cells that have been found in the bronchoalveolar lavage fluid and sputum of patients are neutrophils and macrophages rather than eosinophils. Elevated levels of inflammatory mediators are also found in COPD patients, including IL-8, $LTB_4$, and $TNF-\alpha$, and the surface epithelium and sub-epithelium of the bronchi of such patients has been found to be infiltrated by T-lymphocytes and macrophages. Symptomatic relief for COPD patients can be provided by the use of β-agonist and anticholinergic bronchodilators, but the progress of the disease remains unaltered. COPD has been treated using theophylline, but without much success, due in part to its propensity to produce unwanted effects. Steroids have also failed to hold out much promise as satisfactory treatment agents in COPD as they are relatively ineffective as anti-inflammatory agents.

Accordingly, the use of the combinations of therapeutic agents of the present invention to treat COPD and its related and included obstructed airways diseases, represents a significant advance in the art. The present invention is not limited to any particular mode of action or any hypothesis as to the way in which the desired therapeutic objectives have been obtained by utilizing the combinations of therapeutic agents of the present invention.

Bronchitis and Bronchiectasis

In accordance with the particular and diverse inhibitory activities described above that are possessed by the combinations of therapeutic agents of the present invention, they are useful in the treatment of bronchitis of whatever type, etiology, or pathogenesis, including, e.g., acute bronchitis which has a short but severe course and is caused by exposure to cold, breathing of irritant substances, or an acute infection; catarrhal bronchitis which is a form of acute bronchitis with a profuse mucopurulent discharge; chronic bronchitis which is a long-continued form of bronchitis with a more or less marked tendency to recurrence after stages of quiescence, due to repeated attacks of acute bronchitis or chronic general diseases, characterized by attacks of coughing, by expectoration either scanty or profuse, and by secondary changes in the lung tissue; dry bronchitis which is characterized by a scanty secretion of tough sputum; infectious asthmatic bronchitis which is a syndrome marked by the development of symptoms of bronchospasm following respiratory tract infections in persons with asthma; productive bronchitis which is bronchitis associated with a productive cough.

The use of the combinations of therapeutic agents of the present invention to treat atopic asthma or non-atopic asthma, COPD or other chronic inflammatory airways diseases may be established and demonstrated by use of a number of different models known in the art of inhibition of reflex events in the airway including plasma extravasation and bronchospasmolytic models described below.

Bronchodilator Activity—cAMP is involved not only in smooth muscle relaxation, but also exerts an overall inhibitory influence on airway smooth muscle proliferation, both of which may result from activation of A2a receptors by a component of the invention. Airway smooth muscle hypertrophy and hyperplasia can be modulated by cAMP, and these conditions are common morphological features of chronic asthma.

The use of the combinations of therapeutic agents of the present invention to treat atopic asthma or non-atopic asthma, COPD or other chronic inflammatory airways diseases may be established and demonstrated by use of a number of different models known in the art including the models described below.

Bronchospasmolytic Activity In Vitro—The ability of the combinations of therapeutic agents of the present invention to cause relaxation of guinea-pig tracheal smooth muscle is demonstrated in the following test procedure. Guinea-pigs (350–500 g) are killed with sodium pentothal (100 mg/kg i.p.). The trachea is dissected and a section 2–3 cm in length is excised. The trachea is transected in the transverse plane at alternate cartilage plates so as to give rings of tissue 3–5 mm in depth. The proximal and distal rings are discarded. Individual rings are mounted vertically on stainless steel supports, one of which is fixed at the base of an organ bath, while the other is attached to an isometric transducer. The rings are bathed in Krebs solution (composition $\mu$M: NaHCO$_3$ 25; NaCl 113; KCl 4.7; MgSO$_4$.7H$_2$O 1.2; KH$_2$PO$_4$ 1.2; CaCl$_2$ 2.5; glucose 11.7) at 37° C. and gassed with O$_2$/CO$_2$ (95:5, v/v). Rings prepared in this manner are contracted by field stimulation. To ascertain spasmolytic activity, test combinations of therapeutic agents of the present invention are dissolved in physiological saline and added in increasing quantities to the organ bath at 5 m intervals to provide a cumulative concentration-effect curve.

In the above test model, combinations of therapeutic agents of the present invention generally inhibit field stimulated contraction of guinea-pig tracheal ring preparations at concentrations in the range of from 0.001 to 1.0 $\mu$M.

Relaxation of Human Bronchus—Samples of human lungs dissected during surgery for cancer are obtained within 3 days after removal. Small bronchi (inner diameter≈2 to 5 mm) are excised, cut into segments and placed in 2 ml liquid nitrogen storage ampoules filled with fetal calf serum (FCS) containing 1.8M dimethylsulfoxide (DMSO) and 0.1M sucrose as cryoprotecting agents. The ampoules are placed in a polystyrol box (11×11×22 cm) and slowly frozen at a mean cooling rate of about 0.6° C./m in a freezer maintained at −70° C. After 3–15 h the ampoules are transferred into liquid nitrogen (−196° C.) where they are stored until use. Before use the tissues are exposed for 30–60 m to −70° C. before being thawed within 2.5 m by placing the ampoules in a 37° C. water bath. Thereafter the bronchial segments are rinsed by placing them in a dish containing Krebs-Henseleit solution ($\mu$M: NaCl 118, KCl 4.7. MgSO$_4$ 1.2, CaCl$_2$ 1.2, KH$_2$PO$_4$ 1.2, NaHCO$_3$ 25, glucose 11, EDTA 0.03) at 37° C., cut into rings and suspended in 10 ml organ baths for isometric tension recording under a preload of about 1 g. Further increases in tension are induced via the application of field stimulation, which is known to induce activation of nerves in the airway sample and generate tension via release of acetylcholine and other neurally derived mediators. Concentration-response curves are produced by cumulative additions, each concentration being added when the maximum effect has been produced by the previous concentration. Papaverine (300 $\mu$M) is added at the end of the concentration response curve to induce complete relaxation of the bronchial rings. This effect is taken as 100% relaxation.

In the above test model the combinations of therapeutic agents of the present invention generally produce concentration-related relaxation of human bronchus ring preparations at concentrations in the range of from 0.001 to 1.0 $\mu$M with preferred embodiments being active at concentrations in the range of from 5.0 nM to 500 nM.

Suppression of Capsaicin-induced Bronchoconstriction—Male Dunkin-Hartley guinea-pigs (400–800 g) having free access to food and water prior to the experiment, are anaesthetized with sodium phenobarbital (100 mg/kg i.p. [intra peritoneal]). Animals, maintained at 37° C. with a heated pad, controlled by a rectal thermometer, are ventilated via a tracheal cannula (about 8 ml/kg, 1 Hz) with a mixture of air and oxygen (45:55 v/v). Ventilation is monitored at the trachea by a pneumotachograph connected to a differential pressure transducer in line with the respiratory pump. Pressure changes within the thorax are monitored directly via an intrathoracic cannula, using a differential pressure transducer so that the pressure difference between the trachea and thorax can be measured and displayed. From these measurements of air-flow and transpulmonary pressure, both airway resistance ($R_1$ cmH$_2$O/l/s) and compliance (Cd$_{dyn}$) are calculated with a digital electronic respiratory analyzer for each respiratory cycle. Blood pressure and heart rate are recorded from the carotid artery using a pressure transducer.

When values for basal resistance and compliance are stable, an acute episode of bronchoconstriction is induced by an intravenous bolus of capsaicin. Capsaicin is dissolved in 100% ethanol and diluted with phosphate buffered saline. Test combinations of therapeutic agents of the present invention are administered when the response to capsaicin is stable, which is calculated to be after 2–3 such administrations at 10 min intervals. Reversal of bronchoconstriction is assessed over 1–8 h following either intratracheal or intraduodenal instillation or intravenous bolus injection. Bronchospasmolytic activity is expressed as a % inhibition of the initial, maximal resistance ($R_D$) following the infusion of capsaicin. ED$_{50}$ values represent the dose which causes a 50% reduction of the increase in resistance induced by capsaicin. Duration of action is defined as the time in minutes where bronchoconstriction is reduced by 50% or more. Effects on blood pressure (BP) and heart rate (HR) are characterized by ED$_{20}$ values; i.e., the doses which reduce BP or HR by 20% measured 5 m after administration.

In the above test model the combinations of therapeutic agents of the present invention generally exhibit bronchodilator activity at dosages in the range of from 0.001 to 0.1 mg/kg i.t. [intra tracheal]. Further, the combination delivered i.t. exhibits an at least additive inhibitory effect on bronchospasm, with each component alone being able to inhibit more than 50% of the observed control response.

LPS-Induced Lung Neutrophilia—The recruitment to and activation of neutrophils in the lungs is considered an important pathological feature in COPD and in severe asthma. Consequently, inhibition of either or both of these endpoints in animals provides supportive evidence of the utility of the present invention.

Male Wistar-Albino rats (150–250 g) or male Dunkin-Hartley guinea-pigs (400–600 g) are pretreated with the test articles alone or in combination by inhalation or intratracheal (i.t.) instillation under brief general anaesthesia. After 1–24 h after compound administration, animals are challenged with an inhalation aerosol of bacterial liopolysaccharide (LPS) sufficient to induce over the subsequent 1–24 h of a pronounced lung neutrophilia. The neutrophilia is assessed by cell counting in bronchial washings or by determination of neutrophil products in lung washings or tissue. In this test system, the therapeutic agents of the present invention generally exhibit anti-inflammatory activity at doses ranging from 0.0001 to 0.1 mg/kg i.t. Unexpectedly, the combination delivered i.t. exerts at least an additive effect on inflammation, despite the fact that one of the components does not on its own exert a significant anti-inflammatory effect. Further, equivalent anti-inflammatory effects of a high dose of one of the components can be observed with lower doses when used in combination as in this invention, thus minimising systemic unwanted effects.

Allergic guinea-pig Assay—A test for evaluating the therapeutic impact of the combinations of therapeutic agents of the present invention on the symptom of dyspnea and bronchspasm i.e., difficult or labored breathing and increased lung resistance, and on the symptom of inflammation, ie: lung neutrophilia and eosinophilia, utilizes Dunkin-Hartley guinea-pigs (400–600 g body weight).

The egg albumin (EA), grade V, crystallized and lyophilized, aluminum hydroxide, and mepyramine maleate used in this test are commercially available. The challenge and subsequent respiratory readings are carried out in a clear plastic box with internal dimensions of 10×6×4 inches. The head and body sections of the box are separable. In use the two are held firmly together by clamps, and an airtight seal between the chambers is maintained by a soft rubber gasket.

Through the centre of the head end of the chamber a nebulizer is inserted via an airtight seal and each end of the box also has an outlet. A pneumotachograph is inserted into one end of the box and is coupled to a volumetric pressure transducer which is then connected to a dynograph through appropriate couplers. While aerosolizing the antigen, the outlets are open and the pneumotachograph is isolated from the chamber. The outlets are then closed and the pneumotachograph and the chamber are connected during the recording of the respiratory patterns. For challenge, 2 ml of a 3% solution of antigen in saline is placed in each nebulizer and the aerosol is generated with air from a small diaphragm pump operating at 10 psi and a flow rate of 8 l/m.

Guinea-pigs are sensitized by injecting subcutaneously and i.p. 1 ml of a suspension containing 1 mg EA and 200 mg aluminum hydroxide in saline. They are used between days 12 and 24 post-sensitization. In order to eliminate the histamine component of the response, guinea-pigs are pretreated i.p. 30 min prior to aerosol challenge with 2 mg/kg of mepyramine. Guinea-pigs are then exposed to an aerosol of 3% EA in saline for exactly 1 m, then respiratory profiles are recorded for a further 30 m. Subsequently, lung inflammation is determined post mortem over a period of 1–48 h. The duration of continuous dyspnea is measured from the respiratory recordings.

Test combinations of therapeutic agents of the present invention are generally administered i.t. or by aerosol 0.5–4 h prior to challenge. The combinations of compounds are either dissolved in saline or biocompatible solvents. The activity of the compounds is determined on the basis of their ability to decrease the magnitude and duration of symptoms of dyspnea and broncospasm and/or magnitude of lung inflammation in comparison to a group of vehicle-treated controls. Tests of the combinations of therapeutic agents of the present invention are evaluated over a series of doses and an $ED_{50}$ is derived that is defined as the dose (mg/kg) which will inhibit the duration of symptoms by 50%.

Anti-inflammatory Activity—The anti-inflammatory activity of the combinations of therapeutic agents of the present invention is demonstrated by the inhibition of eosinophil or neutrophil activation. In this assay blood samples (50 ml) are collected from non-atopic volunteers with eosinophil numbers ranging between 0.06 and $0.47 \times 10^9$ $L^{-1}$. Venous blood is collected into centrifuge tubes containing 5 ml trisodium citrate (3.8%, pH 7.4).

The anticoagulated blood is diluted (1:1, v:v) with phosphate-buffered saline (PBS, containing neither calcium nor magnesium) and is layered onto 15 ml isotonic Percoll (density 1.082–1.085 g/ml, pH 7.4), in a 50 ml centrifuge tube. Following centrifugation (30 minutes, 1000×g, 20° C.), mononuclear cells at the plasma/Percoll interface are aspirated carefully and discarded.

The neutrophil/eosinophil/erythrocyte pellet (ca. 5 ml by volume) is gently resuspended in 35 ml of isotonic ammonium chloride solution ($NH_4Cl$, 155 mM; $KHCO_3$, 10 mM; EDTA. 0.1 mM; 0–4° C.). After 15 min, cells are washed twice (10 min, 400×g, 4° C.) in PBS containing fetal calf serum (2%, FCS).

A magnetic cell separation system is used to separate eosinophils and neutrophils. This system is able to separate cells in suspension according to surface markers, and comprises a permanent magnet, into which is placed a column that includes a magnetizable steel matrix. Prior to use, the column is equilibrated with PBS/FCS for 1 hour and then flushed with ice-cold PBS/FCS on a retrograde basis via a 20 ml syringe. A 21G hypodermic needle is attached to the base of the column and 1–2 ml of ice cold buffer are allowed to efflux through the needle.

Following centrifugation of granulocytes, supernatant is aspirated and cells are gently resuspended with 100 µl magnetic particles (anti-CD16 monoclonal antibody, conjugated to superparamagnetic particles). The eosinophil/neutrophil/anti-CD16 magnetic particle mixture is incubated on ice for 40 minutes and then diluted to 5 ml with ice-cold PBS/FCS. The cell suspension is slowly introduced into the top of the column and the tap is opened to allow the cells to move slowly into the steel matrix. The column is then washed with PBS/FCS (35 ml), which is carefully added to the top of the column so as not to disturb the magnetically labeled neutrophils already trapped in the steel matrix.

Non-labeled eosinophils are collected in a 50 ml centrifuge tube and washed (10 minutes, 400×g, 4° C.). The resulting pellet is resuspended in 5 ml Hank's balanced salt solution (HBSS) so that cell numbers and purity can be assessed prior to use. The separation column is removed from the magnet and the neutrophil fraction is eluted. The column is then washed with PBS (50 ml) and ethanol (absolute), and stored at 4° C.

Total cells are counted with a micro cell counter. One drop of lysogenic solution is added to the sample, which after 30 s is recounted to assess contamination with erythrocytes. Cytospin smears are prepared on a Shandon Cytospin 2 cytospinner (100 µl samples, 3 minutes, 500 rpm). These preparations are stained and differential cell counts are determined by light microscopy, examining at least 500 cells. Cell viability is assessed by exclusion of trypan blue.

Eosinophils or neutrophils are diluted in HBSS and pipetted into 96 well microtiter plates (MTP) at $1-10 \times 10^3$ cells/well. Each well contains a 200 µl sample comprising: 100 µl cell suspension; 50 µl HBSS; 10 µl lucigenin; 20 µl activation stimulus; and 20 µl test compound.

The samples are incubated with test compound or vehicle for 10 m prior to addition of an activation stimulus fMLP (1–10 µM) or C5a (1–100 nM) dissolved in dimethylsulfoxide and thereafter diluted in buffer, such that the highest solvent concentration used is 1% (at 100 µM test compound). MTPs are agitated to facilitate mixing of the cells and medium, and the MTP is placed into a luminometer. Total chemiluminescence and the temporal profile of each well is measured simultaneously over 20 m and the results expressed as arbitrary units, or as a percentage of fMLP-induced chemiluminescence in the absence of test compound. Results are fitted to the Hill equation and $IC_{50}$ values are calculated automatically.

The combinations of therapeutic agents of the present invention are generally active in the above test method at concentrations in the range of from 0.0001 µM to 0.5 µM, with preferred embodiments being active at concentrations in the range of from 0.1 nM to 100 nM.

The anti-inflammatory activity of the combinations of therapeutic agents of the present invention is additionally demonstrated by the inhibition of plasma extravasation into rat airways. In this assay tracheal tissue is taken and the extent of plasma leakage determined. This assay relates equally to other chronic inflammatory diseases of the airways including but not limited to COPD and accordingly is not recapitulated in that section.

Wistar albino rats (150–200 g) or Dunkin-Hartley guinea-pigs (450–600 g) are anaesthetised with sodium pentobarbitone and venous and arterial cannulae installed. Evans Blue dye to bind plasma proteins is administered i.v. (30 mg/kg). After 10 mins the test agents are administered i.t. and 10 mins later capsaicin administered i.v. (3 ug/kg). 30 mins later, tracheal tissue is removed, extracted overnight into formamide and absorbance read at 620 nm. In some experiments the order of dosing was reversed such that the compounds were administered before the Evans Blue and inflammatory stimulus.

In the above test model the combinations of therapeutic agents of the present invention generally exhibit anti-inflammatory activity at dosages in the range of from 0.001 to 0.1 mg/kg i.t.

From the above it may be seen that the combinations of therapeutic agents of the present invention are useful for the treatment of inflammatory or obstructive airways diseases or other conditions involving airways obstruction. In particular they are useful for the treatment of bronchial asthma.

In view of their anti-inflammatory activity and their influence on airways hyper-reactivity, the combinations of therapeutic agents of the present invention are useful for the treatment, in particular prophylactic treatment, of obstructive or inflammatory airways diseases. Thus, by continued and regular administration over prolonged periods of time the combinations of compounds of the present invention are useful in providing advance protection against the recurrence of bronchoconstriction or other symptomatic attack consequential to obstructive or inflammatory airways diseases. The combinations of compounds of the present invention are also useful for the control, amelioration or reversal of the basal status of such diseases.

Having regard to their bronchodilator activity the combinations of therapeutic agents of the present invention are useful as bronchodilators, e.g., in the treatment of chronic or acute bronchoconstriction, and for the symptomatic treatment of obstructive or inflammatory airways diseases.

Obstructive or inflammatory airways diseases to which the present invention applies include asthma; pneumoconiosis; chronic eosinophilic pneumonia; chronic obstructive airways or pulmonary disease (COAD or COPD); and adult respiratory distress syndrome (ARDS), as well as exacerbation of airways hyper-reactivity consequent to other drug therapy, e.g., aspirin or β-agonist therapy.

The adenosine $A_{2a}$ receptor agonists and adrenergic β2 receptor agonists of the present invention can be administered alone or in combination but will generally be administered in admixture with a suitable pharmaceutical excipient, diluent or carrier.

The adenosine $A_{2a}$ receptor agonists and adrenergic β2 receptor agonists of the present invention are preferably administered by inhalation and are conveniently delivered in the form of a dry powder (either alone or as a mixture, for example a mixture with lactose) from a dry powder inhaler or an aerosol spray presentation from a pressurised container, pump, spray, atomiser (preferably an atomiser using electrohydrodynamics to produce a fine mist) or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide, a further perfluorinated hydrocarbon such as Perflubron (trade mark) or other suitable gas.

In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol (optionally, aqueous ethanol) or a suitable agent for dispersing, solubilising or extending release and the propellant as the solvent, which may additionally contain a lubricant, e.g. sorbitan trioleate. Capsules, blisters and cartridges (made, for example, from gelatin or HPMC) for use in an inhaler or insufflator may be formulated to contain a powder mix of the compound of the invention, a suitable powder base such as lactose or starch and a performance modifier such as I-leucine, mannitol or magnesium stearate.

Prior to use in a dry powder formulation or suspension formulation for inhalation the compound of the invention will be micronised to a size suitable for delivery by inhalation (typically considered as less than 5 microns). Micronisation could be achieved by a range of methods, for example spiral jet milling, fluid bed jet milling or use of supercritical fluid crystallisation.

A suitable solution formulation for use in an atomiser using electrohydrodynamics to produce a fine mist may contain from 1 µg to 10 mg of the compound of the invention per actuation and the actuation volume may vary from 1 to 100 µl. A typical formulation may comprise a compound of the invention, propylene glycol, sterile water, ethanol and sodium chloride. Alternative solvents may be used in place of propylene glycol, for example glycerol or polyethylene glycol.

Aerosol or dry powder formulations are preferably arranged so that each metered dose or "puff" contains from 1 to 4000 µg of a compound of the invention for delivery to the patient. The overall daily dose with an aerosol will be in the range of from 1 µg to 20 mg which may be administered in a single dose or, more usually, in divided doses throughout the day.

The preferred ratio, by weight (w/w), of adenosine $A_{2a}$ receptor agonist: adrenergic β2 receptor agonist used will depend on the particular combination being examined. This is due to differences in the potency of individual compounds. The physician in any event will determine the actual dosage of each compound which will be most suitable for any individual patient and it will vary with the age, weight and response of the particular patient.

It is to be appreciated that all references herein to treatment include curative, palliative and prophylactic treatment.

I claim:

1. A combination comprising (a) an adenosine $A_{2a}$ receptor agonist of formula (I):

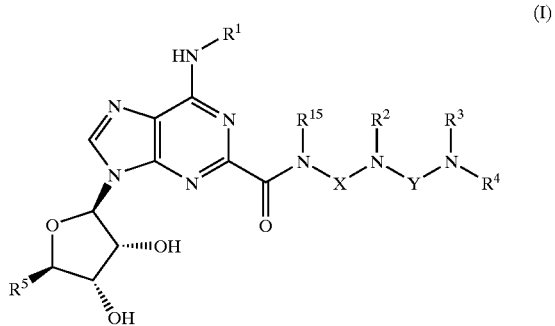

or a pharmaceutically acceptable salt or solvate thereof, wherein $R^1$ is H, $C_1$–$C_6$ alkyl or fluorenyl, said $C_1$–$C_6$ alkyl being optionally substituted by 1 or 2 substituents each independently selected from phenyl and naphthyl, said phenyl and naphthyl being optionally substituted by $C_1$–$C_6$ alkyl, $C_1$–$C_6$ alkoxy, halo or cyano;

(A) $R^2$ is H or $C_1$–$C_6$ alkyl, $R^{15}$ is H or $C_1$–$C_6$ alkyl, and X is either (i) unbranched $C_2$–$C_3$ alkylene optionally substituted by $C_1$–$C_6$ alkyl or $C_3$–$C_8$ cycloalkyl, or (ii) a group of the formula:

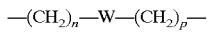

—(CH$_2$)$_n$—W—(CH$_2$)$_p$— where W is $C_5$–$C_7$ cycloalkylene optionally substituted by $C_1$–$C_6$ alkyl, n is 0 or 1 and p is 0 or 1, or (B) $R^{15}$ is H or $C_1$–$C_6$ alkyl, and $R^2$ and X, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl, or (C) $R^2$ is H or $C_1$–$C_6$ alkyl, and $R^{15}$ and X, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl;

either, $R^3$ and $R^4$, taken together with the nitrogen atom to which they are attached, represent azetidinyl, pyrrolidinyl, piperidinyl, piperazinyl, homopiperidinyl or homopiperazinyl, each being optionally substituted on a ring nitrogen or carbon atom by $C_1$–$C_6$ alkyl or $C_3$–$C_8$ cycloalkyl and optionally substituted on a ring carbon atom not adjacent to a ring nitrogen atom by —NR$^6$R$^7$, or, $R^3$ is H, $C_1$–$C_6$ alkyl, $C_3$–$C_8$ cycloalkyl or benzyl and $R^4$ is (a) azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl, $C_3$–$C_8$ cycloalkyl, phenyl, benzyl or het, or (b) —($C_2$–$C_6$ alkylene)-$R^8$, (c) —($C_1$–$C_6$ alkylene)-$R^{13}$, or (d) $C_1$–$C_6$ alkyl or $C_3$–$C_8$ cycloalkyl;

$R^5$ is $CH_2OH$ or $CONR^{14}R^{14}$;

$R^6$ and $R^7$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl;

$R^8$ is (i) azetidin-1-yl, pyrrolidin-1-yl, piperidin-1-yl, morpholin-4-yl, piperazin-1-yl, homopiperidin-1-yl, homopiperazin-1-yl or tetrahydroisoquinolin-1-yl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^9R^9N$—($C_1$–$C_6$)-alkyl, fluoro-($C_1$–$C_6$)-alkyl, —CONR$^9$R$^9$, —COOR$^9$ or $C_2$–$C_5$ alkanoyl, and optionally substituted on a ring carbon atom not adjacent to a ring nitrogen atom by fluoro-($C_1$–$C_6$)-alkoxy, halo, —OR$^9$, cyano, —S(O)$_m$R$^{10}$, —NR$^9$R$^9$, —SO$_2$NR$^9$R$^9$, —NR$^9$COR$^{10}$ or —NR$^9$SO$_2$R$^{10}$, and said piperazin-1-yl and homopiperazin-1-yl being optionally substituted on the ring nitrogen atom not attached to the $C_2$–$C_6$ alkylene group by $C_1$–$C_6$ alkyl, phenyl, $C_1$–$C_6$ alkoxy-($C_2$–$C_6$)-alkyl, $R^9R^9N$—($C_2$–$C_6$)-alkyl, fluoro-($C_1$–$C_6$)-alkyl, $C_2$–$C_5$ alkanoyl, —COOR$^{10}$, $C_3$–$C_8$ cycloalkyl, —SO$_2$R$^{10}$, —SO$_2$NR$^9$R$^9$ or —CONR$^9$R$^9$, or (ii) NR$^{11}$R$^{12}$;

$R^9$ is H, $C_1$–$C_6$ alkyl, $C_3$–$C_8$ cycloalkyl or phenyl;

$R^{10}$ is $C_1$–$C_6$ alkyl, $C_3$–$C_8$ cycloalkyl or phenyl;

$R^{11}$ is H, $C_1$–$C_6$ alkyl, $C_3$–$C_8$ cycloalkyl or benzyl;

$R^{12}$ is H, $C_1$–$C_6$ alkyl, $C_3$–$C_8$ cycloalkyl, phenyl, benzyl, fluoro-($C_1$–$C_6$)-alkyl, —CONR$^9$R$^9$, —COOR$^{10}$, $C_2$–$C_5$ alkanoyl or —SO$_2$NR$^9$R$^9$;

$R^{13}$ is (a) phenyl, pyridin-2-yl, pyridin-3-yl or pyridin-4-yl, each being optionally substituted by $C_1$–$C_6$ alkyl, $C_1$–$C_6$ alkoxy, —($C_1$–$C_3$ alkylene)-($C_1$–$C_6$ alkoxy), halo, cyano, —($C_1$–$C_3$ alkylene)-CN, —CO$_2$H, —($C_1$–$C_3$ alkylene)-CO$_2$H, —CO$_2$($C_1$–$C_6$ alkyl), —($C_1$–$C_3$ alkylene)-CO$_2$($C_1$–$C_6$ alkyl), —($C_1$–$C_3$ alkylene)-NR$^{14}$R$^{14}$, —CONR$^{14}$R$^{14}$ or —($C_1$–$C_3$ alkylene)-CONR$^{14}$R$^{14}$, or (b) azetidin-2-yl, azetidin-3-yl, pyrrolidin-2-yl, pyrrolidin-3-yl, piperidin-2-yl, piperidin-3-yl, piperidin-4-yl, homopiperidin-2-yl, homopiperidin-3-yl or homopiperidin-4-yl, each being optionally substituted by $C_1$–$C_6$ alkyl, $C_3$–$C_8$ cycloalkyl, phenyl, benzyl or het;

$R^{14}$ is H or $C_1$–$C_6$ alkyl optionally substituted by cyclopropyl;

m is 0, 1 or 2;

Y is CO, CS, SO$_2$ or C=N(CN); and het is a C-linked, 4- to 6-membered ring, heterocycle having either from 1 to 4 ring nitrogen heteroatoms or 1 or 2 nitrogen ring heteroatoms and 1 oxygen or 1 sulphur ring heteroatom, optionally substituted by $C_1$–$C_6$ alkyl, $C_3$–$C_8$ cycloalkyl, $C_1$–$C_6$ alkoxy, $C_3$–$C_8$ cycloalkoxy, hydroxy, oxo or halo;

and (b) an adrenergic β2 receptor agonist.

2. The combination of claim 1 wherein the adenosine $A_{2a}$ receptor agonist of the formula (I) is 6-[(2,2-diphenylethyl)amino]-9-{(2R,3R,4S,5S)-5-[(ethylamino)carbonyl]-3,4-dihydroxytetrahydro-2-furanyl}-N-{2-[({[1-(2-pyridinyl)-4-piperidinyl]amino}carbonyl)amino]ethyl}-9H-purine-2-carboxamide or a pharmaceutically acceptable salt or solvate thereof.

3. A combination of claim 1 wherein the adrenergic β2 receptor agonist is salmeterol or a pharmaceutically acceptable salt or solvate thereof.

4. A combination of claim 1 wherein the adrenergic β2 receptor agonist is formoterol or a pharmaceutically acceptable salt or solvate thereof.

5. A combination of claim 2 wherein the adrenergic β2 receptor agonist is salmeterol or a pharmaceutically acceptable salt or solvate thereof.

6. A combination of claim 2 wherein the adrenergic β2 receptor agonist is formoterol or a pharmaceutically acceptable salt or solvate thereof.

7. A pharmaceutical composition comprising an adenosine $A_{2a}$ receptor agonist of formula (I),

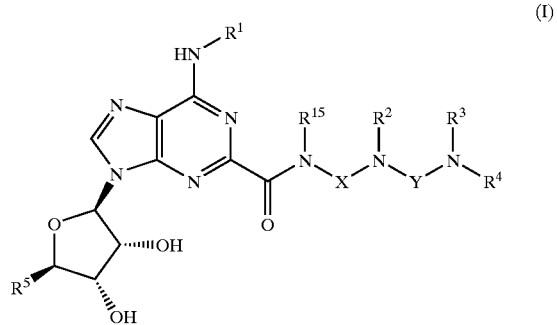

or a pharmaceutically acceptable salt or solvate thereof, wherein $R^1$ is H, $C_1$–$C_6$ alkyl or fluorenyl, said $C_1$–$C_6$ alkyl being optionally substituted by 1 or 2 substituents each independently selected from phenyl and naphthyl, said phenyl and naphthyl being optionally substituted by $C_1$–$C_6$ alkyl, $C_1$–$C_6$ alkoxy, halo or cyano;

(A) $R^2$ is H or $C_1$–$C_6$ alkyl, $R^{15}$ is H or $C_1$–$C_6$ alkyl, and X is either (i) unbranched $C_2$–$C_3$ alkylene optionally substituted by $C_1$–$C_6$ alkyl or $C_3$–$C_8$ cycloalkyl, or (ii) a group of the formula:

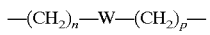

where W is $C_5$–$C_7$ cycloalkylene optionally substituted by $C_1$–$C_6$ alkyl, n is 0 or 1 and p is 0 or 1, or (B) $R^{15}$ is H or $C_1$–$C_6$ alkyl, and $R^2$ and X, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl, or (C) $R^2$ is H or $C_1$–$C_6$ alkyl, and $R^{15}$ and X, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl;

either, $R^3$ and $R^4$, taken together with the nitrogen atom to which they are attached, represent azetidinyl, pyrrolidinyl, piperidinyl, piperazinyl, homopiperidinyl or homopiperazinyl, each being optionally substituted on a ring nitrogen or carbon atom by $C_1$–$C_6$ alkyl or $C_3$–$C_8$ cycloalkyl and optionally substituted on a ring carbon atom not adjacent to a ring nitrogen atom by —$NR^6R^7$, or, $R^3$ is H, $C_1$–$C_6$ alkyl, $C_3$–$C_8$ cycloalkyl or benzyl and $R^4$ is (a) azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl, $C_3$–$C_8$ cycloalkyl, phenyl, benzyl or het, or (b) —($C_2$–$C_6$ alkylene)-$R^8$, (c) —($C_1$–$C_6$ alkylene)-$R^{13}$, or (d) $C_1$–$C_6$ alkyl or $C_3$–$C_8$ cycloalkyl;

$R^5$ is $CH_2OH$ or $CONR^{14}R^{14}$;

$R^6$ and $R^7$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl;

$R^8$ is (i) azetidin-1-yl, pyrrolidin-1-yl, piperidin-1-yl, morpholin-4-yl, piperazin-1-yl, homopiperidin-1-yl, homopiperazin-1-yl or tetrahydroisoquinolin-1-yl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^9R^9N$—($C_1$–$C_6$)-alkyl, fluoro-($C_1$–$C_6$)-alkyl, —$CONR^9R^9$, —$COOR^9$ or $C_2$–$C_5$ alkanoyl, and optionally substituted on a ring carbon atom not adjacent to a ring nitrogen atom by fluoro-($C_1$–$C_6$)-alkoxy, halo, —$OR^9$, cyano, —$S(O)_mR^{10}$, —$NR^9R^9$, —$SO_2NR^9R^9$, —$NR^9COR^{10}$ or —$NR^9SO_2R^{10}$, and said piperazin-1-yl and homopiperazin-1-yl being optionally substituted on the ring nitrogen atom not attached to the $C_2$–$C_6$ alkylene group by $C_1$–$C_6$ alkyl, phenyl, $C_1$–$C_6$ alkoxy-($C_2$–$C_6$)-alkyl, $R^9R^9N$—($C_2$–$C_6$)-alkyl, fluoro-($C_1$–$C_6$)-alkyl, $C_2$–$C_5$ alkanoyl, —$COOR^{10}$, $C_3$–$C_8$ cycloalkyl, —$SO_2R^{10}$, —$SO_2NR^9R^9$ or —$CONR^9R^9$, or (ii) $NR^{11}R^{12}$;

$R^9$ is H, $C_1$–$C_6$ alkyl, $C_3$–$C_8$ cycloalkyl or phenyl;

$R^{10}$ is $C_1$–$C_6$ alkyl, $C_3$–$C_8$ cycloalkyl or phenyl;

$R^{11}$ is H, $C_1$–$C_6$ alkyl, $C_3$–$C_8$ cycloalkyl or benzyl;

$R^{12}$ is H, $C_1$–$C_6$ alkyl, $C_3$–$C_8$ cycloalkyl, phenyl, benzyl, fluoro-($C_1$–$C_6$)-alkyl, —$CONR^9R^9$, —$COOR^{10}$, $C_2$–$C_5$ alkanoyl or —$SO_2NR^9R^9$;

$R^{13}$ is (a) phenyl, pyridin-2-yl, pyridin-3-yl or pyridin-4-yl, each being optionally substituted by $C_1$–$C_6$ alkyl, $C_1$–$C_6$ alkoxy, —($C_1$–$C_3$ alkylene)-($C_1$–$C_6$ alkoxy), halo, cyano, —($C_1$–$C_3$ alkylene)-CN, —$CO_2H$, —($C_1$–$C_3$ alkylene)-$CO_2H$, —$CO_2$($C_1$–$C_6$ alkyl), —($C_1$–$C_3$ alkylene)-$CO_2$($C_1$–$C_6$ alkyl), —($C_1$–$C_3$ alkylene)-$NR^{14}R^{14}$, —$CONR^{14}R^{14}$ or —($C_1$–$C_3$ alkylene)-$CONR^{14}R^{14}$, or (b) azetidin-2-yl, azetidin-3-yl, pyrrolidin-2-yl, pyrrolidin-3-yl, piperidin-2-yl, piperidin-3-yl, piperidin-4-yl, homopiperidin-2-yl, homopiperidin-3-yl or homopiperidin-4-yl, each being optionally substituted by $C_1$–$C_6$ alkyl, $C_3$–$C_8$ cycloalkyl, phenyl, benzyl or het;

$R^{14}$ is H or $C_1$–$C_6$ alkyl optionally substituted by cyclopropyl;

m is 0, 1 or 2;

Y is CO, CS, $SO_2$ or C=N(CN); and het is a C-linked, 4- to 6-membered ring, heterocycle having either from 1 to 4 ring nitrogen heteroatoms or 1 or 2 nitrogen ring heteroatoms and 1 oxygen or 1 sulphur ring heteroatom, optionally substituted by $C_1$–$C_6$ alkyl, $C_3$–$C_8$ cycloalkyl, $C_1$–$C_6$ alkoxy, $C_3$–$C_8$ cycloalkoxy, hydroxy, oxo or halo;

an adrenergic β2 receptor agonist and a pharmaceutically acceptable excipient, diluent or carrier.

8. A pharmaceutical composition of claim 7 wherein the adenosine $A_{2a}$ receptor agonist of the formula (I) is 6-[(2,2-diphenylethyl)amino]-9-{(2R,3R,4S,5S)-5-[(ethylamino)carbonyl]-3,4-dihydroxytetrahydro-2-furanyl}-N-{2-[({[1-(2-pyridinyl)-4-piperidinyl]amino}carbonyl)amino]ethyl}-9H-purine-2-carboxamide or a pharmaceutically acceptable salt or solvate thereof.

9. A pharmaceutical composition of claim 7 wherein the adrenergic β2 receptor agonist is salmeterol or a pharmaceutically acceptable salt or solvate thereof.

10. A pharmaceutical composition of claim 7 wherein the adrenergic β2 receptor agonist is formoterol or a pharmaceutically acceptable salt or solvate thereof.

11. A pharmaceutical composition of claim 8 wherein the adrenergic β2 receptor agonist is salmeterol or a pharmaceutically acceptable salt or solvate thereof.

12. A pharmaceutical composition of claim 8 wherein the adrenergic β2 receptor agonist is formoterol or a pharmaceutically acceptable salt or solvate thereof.

13. A method of treating an obstructive airways disease in a mammal, said method comprising administering, to said mammal in need of such treatment an effective amount of a composition comprising an adenosine $A_{2a}$ receptor agonist of formula (I),

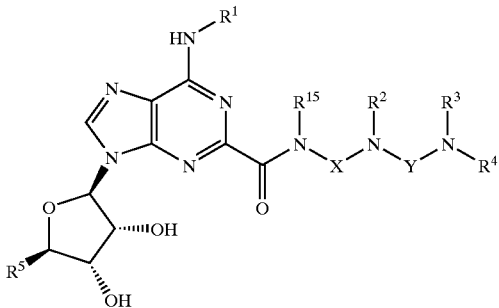

(I)

or a pharmaceutically acceptable salt or solvate thereof, wherein $R^1$ is H, $C_1$–$C_6$ alkyl or fluorenyl, said $C_1$–$C_6$ alkyl being optionally substituted by 1 or 2 substituents each independently selected from phenyl and naphthyl, said phenyl and naphthyl being optionally substituted by $C_1$–$C_6$ alkyl, $C_1$–$C_6$ alkoxy, halo or cyano;

(A) $R^2$ is H or $C_1$–$C_6$ alkyl, $R^{15}$ is H or $C_1$–$C_6$ alkyl, and X is either (i) unbranched $C_2$–$C_3$ alkylene optionally substituted by $C_1$–$C_6$ alkyl or $C_3$–$C_8$ cycloalkyl, or (ii) a group of the formula:

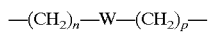

where W is $C_5$–$C_7$ cycloalkylene optionally substituted by $C_1$–$C_6$ alkyl, n is 0 or 1 and p is 0 or 1, or (B) $R^{15}$ is H or $C_1$–$C_6$ alkyl, and $R^2$ and X, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl, or (C) $R^2$ is H or $C_1$–$C_6$ alkyl, and $R^{15}$ and X, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl;

either, $R^3$ and $R^4$, taken together with the nitrogen atom to which they are attached, represent azetidinyl, pyrrolidinyl, piperidinyl, piperazinyl, homopiperidinyl or homopiperazinyl, each being optionally substituted on a ring nitrogen or carbon atom by $C_1$–$C_6$ alkyl or $C_3$–$C_8$ cycloalkyl and optionally substituted on a ring carbon atom not adjacent to a ring nitrogen atom by —$NR^6R^7$, or, $R^3$ is H, $C_1$–$C_6$ alkyl, $C_3$–$C_8$ cycloalkyl or benzyl and $R^4$ is (a) azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl, $C_3$–$C_8$ cycloalkyl, phenyl, benzyl or het, or (b) —($C_2$–$C_6$ alkylene)-$R^8$, (c) —($C_1$–$C_6$ alkylene)-$R^{13}$, or (d) $C_1$–$C_6$ alkyl or $C_3$–$C_8$ cycloalkyl;

$R^5$ is $CH_2OH$ or $CONR^{14}R^{14}$;

$R^6$ and $R^7$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl;

$R^8$ is (i) azetidin-1-yl, pyrrolidin-1-yl, piperidin-1-yl, morpholin-4-yl, piperazin-1-yl, homopiperidin-1-yl, homopiperazin-1-yl or tetrahydroisoquinolin-1-yl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^9R^9N$—($C_1$–$C_6$)-alkyl, fluoro-($C_1$–$C_6$)-alkyl, —$CONR^9R^9$, —$COOR^9$ or $C_2$–$C_5$ alkanoyl, and optionally substituted on a ring carbon atom not adjacent to a ring nitrogen atom by fluoro-($C_1$–$C_6$)-alkoxy, halo, —$OR^9$, cyano, —$S(O)_mR^{10}$, —$NR^9R^9$, —$SO_2NR^9R^9$, —$NR^9COR^{10}$ or —$NR^9SO_2R^{10}$, and said piperazin-1-yl and homopiperazin-1-yl being optionally substituted on the ring nitrogen atom not attached to the $C_2$–$C_6$ alkylene group by $C_1$–$C_6$ alkyl, phenyl, $C_1$–$C_6$ alkoxy-($C_2$–$C_6$)-alkyl, $R^9R^9N$—($C_2$–$C_6$)-alkyl, fluoro-($C_1$–$C_6$)-alkyl, $C_2$–$C_5$ alkanoyl, —$COOR^{10}$, $C_3$–$C_8$ cycloalkyl, —$SO_2R^{10}$, —$SO_2NR^9R^9$ or —$CONR^9R^9$, or (ii) $NR^{11}R^{12}$;

$R^9$ is H, $C_1$–$C_6$ alkyl, $C_3$–$C_8$ cycloalkyl or phenyl;

$R^{10}$ is $C_1$–$C_6$ alkyl, $C_3$–$C_8$ cycloalkyl or phenyl;

$R^{11}$ is H, $C_1$–$C_6$ alkyl, $C_3$–$C_8$ cycloalkyl or benzyl;

$R^{12}$ is H, $C_1$–$C_6$ alkyl, $C_3$–$C_8$ cycloalkyl, phenyl, benzyl, fluoro-($C_1$–$C_6$)-alkyl, —$CONR^9R^9$, —$COOR^{10}$, $C_2$–$C_5$ alkanoyl or —$SO_2NR^9R^9$;

$R^{13}$ is (a) phenyl, pyridin-2-yl, pyridin-3-yl or pyridin-4-yl, each being optionally substituted by $C_1$–$C_6$ alkyl, $C_1$–$C_6$ alkoxy, —($C_1$–$C_3$ alkylene)-($C_1$–$C_6$ alkoxy), halo, cyano, —($C_1$–$C_3$ alkylene)-CN, —$CO_2H$, —($C_1$–$C_3$ alkylene)-$CO_2H$, —$CO_2$($C_1$–$C_6$ alkyl), —($C_1$–$C_3$ alkylene)-$CO_2$($C_1$–$C_6$ alkyl), —($C_1$–$C_3$ alkylene)-$NR^{14}R^{14}$, —$CONR^{14}R^{14}$ or —($C_1$–$C_3$ alkylene)-$CONR^{14}R^{14}$, or (b) azetidin-2-yl, azetidin-3-yl, pyrrolidin-2-yl, pyrrolidin-3-yl, piperidin-2-yl, piperidin-3-yl, piperidin-4-yl, homopiperidin-2-yl, homopiperidin-3-yl or homopiperidin-4-yl, each being optionally substituted by $C_1$–$C_6$ alkyl, $C_3$–$C_8$ cycloalkyl, phenyl, benzyl or het;

$R^{14}$ is H or $C_1$–$C_6$ alkyl optionally substituted by cyclopropyl;

m is 0, 1 or 2;

Y is CO, CS, $SO_2$ or C=N(CN); and het is a C-linked, 4- to 6-membered ring, heterocycle having either from 1 to 4 ring nitrogen heteroatoms or 1 or 2 nitrogen ring heteroatoms and 1 oxygen or 1 sulphur ring heteroatom, optionally substituted by $C_1$–$C_6$ alkyl, $C_3$–$C_8$ cycloalkyl, $C_1$–$C_6$ alkoxy, $C_3$–$C_8$ cycloalkoxy, hydroxy, oxo or halo;

and an adrenergic β2 receptor agonist.

14. A method of claim 13 wherein the adenosine $A_{2a}$ receptor agonist of the formula (I) is 6-[(2,2-diphenylethyl)amino]-9-{(2R,3R,4S,5S)-5-[(ethylamino)carbonyl]-3,4-dihydroxytetrahydro-2-furanyl}-N-{2-[({[1-(2-pyridinyl)-4-piperidinyl]amino}carbonyl)amino]ethyl}-9H-purine-2-carboxamide or a pharmaceutically acceptable salt or solvate thereof.

15. A method of claim 13 wherein the adrenergic β2 receptor agonist is salmeterol or a pharmaceutically acceptable salt or solvate thereof.

16. A method of claim 13 wherein the adrenergic β2 receptor agonist is formoterol or a pharmaceutically acceptable salt or solvate thereof.

17. A method of claim 14 wherein the adrenergic β2 receptor agonist is salmeterol or a pharmaceutically acceptable salt or solvate thereof.

18. A method of claim 14 wherein the adrenergic β2 receptor agonist is formoterol or a pharmaceutically acceptable salt or solvate thereof.

19. A method of any one of claims 13–18 wherein said adenosine $A_{2a}$ receptor agonist and said adrenergic β2 receptor agonist are administered simultaneously, sequentially or separately.

20. A method of any one of claims 13–18 wherein said obstructive airways disease is asthma, acute respiratory distress syndrome, chronic pulmonary inflammatory disease, bronchitis, chronic bronchitis, chronic pulmonary obstructive disease or silicosis.

21. A method of claim 20 wherein said obstructive airways disease is chronic obstructive pulmonary disease.

22. A method of any one of claims 13–18 wherein said obstructive airways disease is allergic rhinitis or chronic sinusitis.

23. A method of treating an inflammatory disease in a mammal said method comprising administering to said mammal in need of such treatment an effective amount of a composition comprising an adenosine $A_{2a}$ receptor agonist of formula (I),

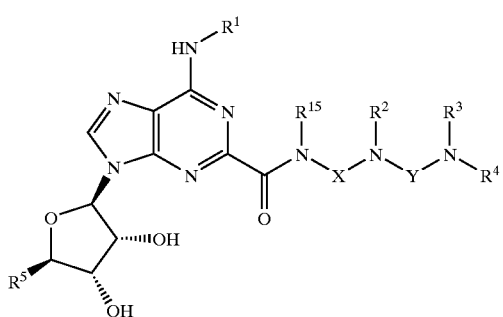

(I)

or a pharmaceutically acceptable salt or solvate thereof, wherein $R^1$ is H, $C_1$–$C_6$ alkyl or fluorenyl, said $C_1$–$C_6$ alkyl being optionally substituted by 1 or 2 substituents each independently selected from phenyl and naphthyl, said phenyl and naphthyl being optionally substituted by $C_1$–$C_6$ alkyl, $C_1$–$C_6$ alkoxy, halo or cyano;

(A) $R^2$ is H or $C_1$–$C_6$ alkyl, $R^{15}$ is H or $C_1$–$C_6$ alkyl, and X is either (i) unbranched $C_2$–$C_3$ alkylene optionally substituted by $C_1$–$C_6$ alkyl or $C_3$–$C_8$ cycloalkyl, or (ii) a group of the formula:

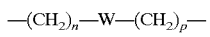

where W is $C_5$–$C_7$ cycloalkylene optionally substituted by $C_1$–$C_6$ alkyl, n is 0 or 1 and p is 0 or 1, or (B) $R^{15}$ is H or $C_1$–$C_6$ alkyl, and $R^2$ and X, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl, or (C) $R^2$ is H or $C_1$–$C_6$ alkyl, and $R^{15}$ and X, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl; either, $R^3$ and $R^4$, taken together with the nitrogen atom to which they are attached, represent azetidinyl, pyrrolidinyl, piperidinyl, piperazinyl, homopiperidinyl or homopiperazinyl, each being optionally substituted on a ring nitrogen or carbon atom by $C_1$–$C_6$ alkyl or $C_3$–$C_8$ cycloalkyl and optionally substituted on a ring carbon atom not adjacent to a ring nitrogen atom by —$NR^6R^7$, or, $R^3$ is H, $C_1$–$C_6$ alkyl, $C_3$–$C_8$ cycloalkyl or benzyl and $R^4$ is (a) azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl, $C_3$–$C_8$ cycloalkyl, phenyl, benzyl or het, or (b) —($C_2$–$C_6$ alkylene)-$R^8$, (c) —($C_1$–$C_6$ alkylene)-$R^{13}$, or (d) $C_1$–$C_6$ alkyl or $C_3$–$C_8$ cycloalkyl;

$R^5$ is $CH_2OH$ or $CONR^{14}R^{14}$;

$R^6$ and $R^7$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl;

$R^8$ is (i) azetidin-1-yl, pyrrolidin-1-yl, piperidin-1-yl, morpholin-4-yl, piperazin-1-yl, homopiperidin-1-yl, homopiperazin-1-yl or tetrahydroisoquinolin-1-yl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^9R^9N$—($C_1$–$C_6$)-alkyl, fluoro-($C_1$–$C_6$)-alkyl, —$CONR^9R^9$, —$COOR^9$ or $C_2$–$C_5$ alkanoyl, and optionally substituted on a ring carbon atom not adjacent to a ring nitrogen atom by fluoro-($C_1$–$C_6$)-alkoxy, halo, —$OR^9$, cyano, —$S(O)_mR^{10}$, —$NR^9R^9$, —$SO_2NR^9R^9$, —$NR^9COR^{10}$ or —$NR^9SO_2R^{10}$, and said piperazin-1-yl and homopiperazin-1-yl being optionally substituted on the ring nitrogen atom not attached to the $C_2$–$C_6$ alkylene group by $C_1$–$C_6$ alkyl, phenyl, $C_1$–$C_6$ alkoxy-($C_2$–$C_6$)-alkyl, $R^9R^9N$—($C_2$–$C_6$)-alkyl, fluoro-($C_1$–$C_6$)-alkyl, $C_2$–$C_5$ alkanoyl, —$COOR^{10}$, $C_3$–$C_8$ cycloalkyl, —$SO_2R^{10}$, —$SO_2NR^9R^9$ or —$CONR^9R^9$, or (ii) $NR^{11}R^{12}$;

$R^9$ is H, $C_1$–$C_6$ alkyl, $C_3$–$C_8$ cycloalkyl or phenyl;

$R^{10}$ is $C_1$–$C_6$ alkyl, $C_3$–$C_8$ cycloalkyl or phenyl;

$R^{11}$ is H, $C_1$–$C_6$ alkyl, $C_3$–$C_8$ cycloalkyl or benzyl;

$R^{12}$ is H, $C_1$–$C_6$ alkyl, $C_3$–$C_8$ cycloalkyl, phenyl, benzyl, fluoro-($C_1$–$C_6$)-alkyl, —$CONR^9R^9$, —$COOR^{10}$, $C_2$–$C_5$ alkanoyl or —$SO_2NR^9R^9$;

$R^{13}$ is (a) phenyl, pyridin-2-yl, pyridin-3-yl or pyridin-4-yl, each being optionally substituted by $C_1$–$C_6$ alkyl, $C_1$–$C_6$ alkoxy, —($C_1$–$C_3$ alkylene)-($C_1$–$C_6$ alkoxy), halo, cyano, —($C_1$–$C_3$ alkylene)-CN, —$CO_2H$, —($C_1$–$C_3$ alkylene)-$CO_2H$, —$CO_2$($C_1$–$C_6$ alkyl), —($C_1$–$C_3$ alkylene)-$CO_2$($C_1$–$C_6$ alkyl), —($C_1$–$C_3$ alkylene)-$NR^{14}R^{14}$, —$CONR^{14}R^{14}$ or —($C_1$–$C_3$ alkylene)-$CONR^{14}R^{14}$, or (b) azetidin-2-yl, azetidin-3-yl, pyrrolidin-2-yl, pyrrolidin-3-yl, piperidin-2-yl, piperidin-3-yl, piperidin-4-yl, homopiperidin-2-yl, homopiperidin-3-yl or homopiperidin-4-yl, each being optionally substituted by $C_1$–$C_6$ alkyl, $C_3$–$C_8$ cycloalkyl, phenyl, benzyl or het;

$R^{14}$ is H or $C_1$–$C_6$ alkyl optionally substituted by cyclopropyl;

m is 0, 1 or 2;

Y is CO, CS, $SO_2$ or C=N(CN); and het is a C-linked, 4- to 6-membered ring, heterocycle having either from 1 to 4 ring nitrogen heteroatoms or 1 or 2 nitrogen ring heteroatoms and 1 oxygen or 1 sulphur ring heteroatom, optionally substituted by $C_1$–$C_6$ alkyl, $C_3$–$C_8$ cycloalkyl, $C_1$–$C_6$ alkoxy, $C_3$–$C_8$ cycloalkoxy, hydroxy, oxo or halo; and an adrenergic β2 receptor agonist.

24. The method of claim 13 wherein said composition is administered by route of inhalation.

25. The method of claim 23 wherein said composition is administered by route of inhalation.

26. The metod of claim 23 wherein the adenosine $A_{2a}$ receptor agonist of the formula (I) is 6-[(2,2-diphenylethyl) amino]-9-{(2R,3R,4S,5S)-5-[(ethylamino)carbonyl]-3,4-dihydroxytetrahydro-2-furanyl}-N-{2-[({[1-(2-pyridinyl)-4-piperidinyl]amino}carbonyl)amino]ethyl}-9H-purine-2-carboxamide or a pharmaceutically acceptable salt or solvate thereof.

27. The method of claim 23 wherein the adrenergic β2 receptor agonist is salmeterol or a pharmaceutically acceptable salt or solvate thereof.

28. The method of claim 23 wherein the adrenergic β2 receptor agonist is formoterol or a pharmaceutically acceptable salt or solvate thereof.

29. The method of claim 26 wherein the adrenergic β2 receptor agonist is salmeterol or a pharmaceutically acceptable salt or solvate thereof.

30. The method of claim 26 wherein the adrenergic β2 receptor agonist is formoterol or a pharmaceutically acceptable salt or solvate thereof.

* * * * *